United States Patent
Noble

(10) Patent No.: US 9,724,198 B2
(45) Date of Patent: Aug. 8, 2017

(54) ORBITAL FLOOR SHEET

(71) Applicant: Poriferous, LLC, Newnan, GA (US)

(72) Inventor: Aaron Noble, Newnan, GA (US)

(73) Assignee: Poriferous, LLC, Newnan, GA (US)

( * ) Notice: Subject to any disclaimer, the term of this patent is extended or adjusted under 35 U.S.C. 154(b) by 0 days.

(21) Appl. No.: 14/802,727

(22) Filed: Jul. 17, 2015

(65) Prior Publication Data

US 2015/0320561 A1    Nov. 12, 2015

Related U.S. Application Data

(60) Provisional application No. 62/025,885, filed on Jul. 17, 2014, provisional application No. 62/051,558, filed on Sep. 17, 2014.

(51) Int. Cl.
| | | |
|---|---|---|
| *A61F 2/02* | (2006.01) | |
| *A61F 2/28* | (2006.01) | |
| *A61F 2/30* | (2006.01) | |

(52) U.S. Cl.
CPC .............. *A61F 2/2846* (2013.01); *A61F 2/28* (2013.01); *A61F 2/2875* (2013.01);
(Continued)

(58) Field of Classification Search
CPC ........ A61F 2/2875; A61F 2/28; A61F 2/2846; A61F 2002/2835; A61F 2002/2878; A61B 17/8085; A61B 17/8071; A61B 17/8076
(Continued)

(56) References Cited

U.S. PATENT DOCUMENTS

| | | | | |
|---|---|---|---|---|
| 4,693,721 A | * | 9/1987 | Ducheyne | ........... A61F 2/30907 |
| | | | | 419/24 |
| 4,976,738 A | * | 12/1990 | Frey | .................... A61F 2/30907 |
| | | | | 623/23.54 |

(Continued)

FOREIGN PATENT DOCUMENTS

| | | |
|---|---|---|
| DE | 199 40 977 A1 | 3/2001 |
| WO | 92/10218 A1 | 6/1992 |
| WO | 2004/093743 | 11/2004 |

OTHER PUBLICATIONS

International Search Report and Written Opinion, PCT Application No. PCT/US2015/040935, mailed Oct. 1, 2015.
(Continued)

*Primary Examiner* — Alvin Stewart
(74) *Attorney, Agent, or Firm* — Kilpatrick Townsend & Stockton LLP

(57) ABSTRACT

Embodiments of the invention described herein thus provide systems and methods for providing improved surgical implants. Embodiments of the implants may include a thin porous sheet formed on a mandrel. The porous sheet that is formed has an interconnected pore structure that may be compressed by a heat compression mold without losing porosity. Additional membrane materials or other layer materials may be applied to one of the face surfaces of the porous sheet or to one of the edges of the porous sheet. For example, a solid membrane surface may be compressed, bonded, welded, or secured a surface face or an edge of the porous sheet. The solid membrane may be compressed or laminated to the upper surface, lower surface, or both. The solid membrane may be welded to at least one edge of the porous sheet (by, for example, being butt welded, thermally bonded, or heat compressed to the at least one edge).

7 Claims, 10 Drawing Sheets

(52) U.S. Cl.
CPC ..... *A61F 2/3094* (2013.01); *A61F 2002/2835* (2013.01); *A61F 2002/2878* (2013.01); *A61F 2002/30011* (2013.01); *A61F 2002/30013* (2013.01); *A61F 2002/3092* (2013.01); *A61F 2002/3096* (2013.01); *A61F 2002/30578* (2013.01); *A61F 2002/30971* (2013.01)

(58) Field of Classification Search
USPC ................. 623/17.18, 17.19, 23.72–23.76
See application file for complete search history.

(56) References Cited

U.S. PATENT DOCUMENTS

| | | | |
|---|---|---|---|
| 6,031,148 A * | 2/2000 | Hayes | A61K 6/0032 600/37 |
| 6,398,814 B1 | 6/2002 | Paasimaa et al. | |
| 7,655,047 B2 | 2/2010 | Swords | |
| 7,901,457 B2 * | 3/2011 | Truncale | A61F 2/28 623/16.11 |
| 7,998,204 B2 * | 8/2011 | Stone | A61L 15/325 424/422 |
| 8,142,886 B2 | 3/2012 | Noble et al. | |
| 8,298,292 B2 | 10/2012 | Swords et al. | |
| 8,398,720 B2 | 3/2013 | Swords | |
| 9,034,315 B2 * | 5/2015 | Geistlich | A61L 15/325 424/93.7 |
| 9,468,512 B2 * | 10/2016 | Koullick | A61F 2/0045 |
| 2001/0010022 A1 * | 7/2001 | Dauner | A61L 27/40 623/23.71 |
| 2002/0013627 A1 * | 1/2002 | Geistlich | A61F 2/30756 623/23.63 |
| 2002/0119177 A1 * | 8/2002 | Bowman | A61L 27/44 424/423 |
| 2003/0039695 A1 * | 2/2003 | Geistlich | A61L 27/24 424/484 |
| 2003/0147935 A1 * | 8/2003 | Binette | A61F 2/0063 424/423 |
| 2004/0237282 A1 * | 12/2004 | Hines | A61F 2/91 29/527.2 |
| 2007/0023131 A1 * | 2/2007 | Farnsworth | A61L 27/52 156/167 |
| 2007/0142914 A1 * | 6/2007 | Jones | A61F 2/30907 623/14.13 |
| 2009/0216338 A1 * | 8/2009 | Gingras | A61F 2/0063 623/23.72 |
| 2010/0215718 A1 | 8/2010 | Swords et al. | |
| 2014/0178455 A1 * | 6/2014 | Nukavarapu | A61L 27/58 424/426 |
| 2015/0320561 A1 * | 11/2015 | Noble | A61F 2/28 623/17.18 |

OTHER PUBLICATIONS

Mok et al., "A Review of Materials Currently Used in Orbital Floor Reconstruction", The Canadian Journal of Plastic Surgeons, 2004, vol. 12, No. 3, pp. 134-140.
International Preliminary Report on Patentability, PCT International Patent Application No. PCT/US2015/040935, mailed Jan. 26, 2017, 7 pages.

* cited by examiner

B-B

ORBITAL FLOOR SHEET

CROSS REFERENCE TO RELATED APPLICATIONS

This application claims the benefit of U.S. Provisional Application Ser. No. 62/025,885, filed Jul. 17, 2014, titled "Orbital Floor and Method for Using Same," and U.S. Provisional Application Ser. No. 62/051,558, filed Sep. 17, 2014, titled "Orbital Floor Sheet," the entire contents of each of which are hereby incorporated by reference.

FIELD OF THE DISCLOSURE

Embodiments of the present disclosure relate generally to surgical materials and implants for use in reconstruction. Certain embodiments of the surgical implants are designed for craniofacial surgery, reconstruction, and/or augmentation. Certain embodiments of the surgical implants are designed for particular use in the orbital floor, and in particular, for orbital reconstructive surgery. Embodiments also relate to methods for using and for manufacturing the surgical implants disclosed.

BACKGROUND

The orbit is the boney socket in the skull that contains and houses the eye, along with the associated structures that support eye function, such as the eye muscles, nerves, and blood vessels. In some instances, a variety of problems can occur in the eye socket, ranging from inflammatory diseases or other diseases, tumors, infections, birth defects, or injuries from trauma. When these problems occur, it may become necessary to reconstruct various portions of the orbital socket, including the orbital floor.

Advances in bone and surgical technology have provided materials that may serve as a substitute for the patient's own tissue, when needed. These advances include titanium plates and screws, hydroxyapatite cement, porous polyethylene, and resorbable fixation devices. However, improvements to surgical implants and materials are desirable.

BRIEF SUMMARY

Embodiments described herein thus provide systems and methods for improved surgical implants. Embodiments of the implants may include a thin porous sheet formed on a mandrel. The porous sheet that is formed has an interconnected pore structure that may be compressed by a heat compression mold without losing porosity. The structure may be one to two particles thick. The interconnected pore structure may have an open pore structure with a pore volume in a 50% range. In one example, the pore range may be from 10-50%. Additional membrane materials or other layer materials may be applied to one of the face surfaces of the porous sheet or to one of the edges of the porous sheet. For example, a solid membrane surface may be compressed, bonded, welded, or secured to a surface face or an edge of the porous sheet. The solid membrane may be compressed or laminated to the upper surface, lower surface, or both. Additionally or alternatively, the solid membrane may be welded to at least one edge of the porous sheet (by, for example, being butt welded, thermally bonded, or heat compressed to the at least one edge). In other embodiments, a porous membrane may be compressed, laminated, welded, or otherwise secured to the thin porous sheet.

Embodiments also relate to methods of forming a surgical implant, comprising: providing a plurality of polymeric particles; heating the particles on a mandrel in order to form a porous sheet with an interconnected pore structure with a thickness of about one to two particles thick; and laminating a solid membrane sheet to a surface of the porous sheet. The method may further include welding a solid membrane sheet to a surface or an edge of the surgical implant. A further a method of forming a surgical implant may comprise: providing a plurality of polymeric particles; heating the particles on a mandrel in order to form a porous sheet with an interconnected pore structure with a thickness of about one to two particles thick; positioning the porous sheet in a mold; applying polymeric material to the porous sheet; and applying compression to the porous sheet and the polymeric material.

DETAILED DESCRIPTION

Embodiments of the present disclosure provide an implant material that may be used for surgical reconstruction. The implant materials may be used to reconstruct bone following fracture, such as trauma. The implant materials may also be used to treat bone deformities caused by disease or birth defects. Specific embodiments have found particular use as an orbital floor sheet, but it should be understood that the materials described herein may be used in other surgical procedures or on other anatomical locations.

The implant sheets described herein may be formed having faces of varying porosities. For example, a first face on one side of the sheet may have a first porosity and a second face on the other side of the sheet may have a second porosity. The first and second faces may both be porous. The first and second faces may have porosities that are similar or the same. The first and second faces may have porosities that are different. In another example, the implant sheet may have a first porous face and a second solid (non-porous) face. In a further example, the implant sheet may have first and second solid (non-porous) faces.

It is also possible for the implant sheets to have varying porosities along the same side. For example, an upper portion of one face may have a first porosity and a lower portion of the same face may have a second porosity. The first and second porosities may be similar or the same. The first and second porosities may be different. In another example, the implant sheet may have a first porous upper portion and a second solid (non-porous) lower portion. In a further example, the implant sheet may have a first solid (non-porous) upper portion and a second porous lower portion. In another example, the upper and lower portions may both be porous. In a further example, the upper and lower portions may both be solid/non-porous. Various permutations of these options are possible. Specific examples are described in more detail below.

As used herein, the term "porous" refers to an interconnected pore structure. As used herein, the term "solid" or "non-porous" refers to a structure without pores and that is impervious to tissue ingrowth.

When used to reconstruct the orbital floor, the thickness of an implant is ideally made as thin as possible so as not to reposition the contents of the orbit. (However, in some cases, a thicker implant may be preferred in order to provide additional volume for positioning a low eye into a more superior position.) The embodiments described herein may be made in varying thicknesses, as described in more detail below. The implant sheets described herein are generally at least partially pliable, while also imparting the desired porosity, if appropriate.

Figure 1:
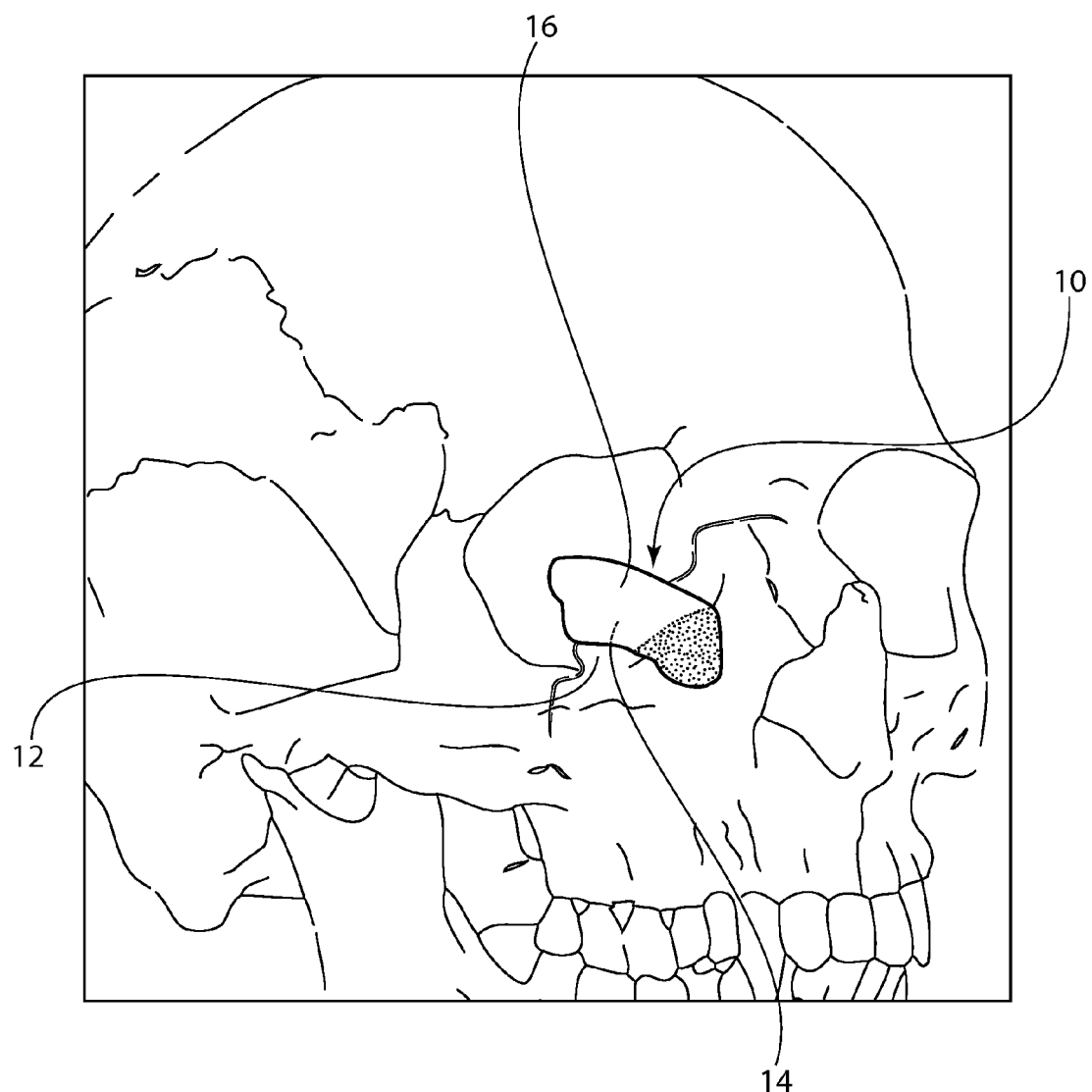
FIG. 1 shows a perspective view of a surgical implant positioned in an orbit.

Generally, for an orbital reconstruction surgery, one side of an implant sheet 10 is positioned against the bone of the patient and an opposite side of the implant sheet faces orbital tissue. One example of an implant sheet 10 positioned on the orbital floor 12 is shown by FIG. 1. As shown, there is a bone-facing side 14 of the sheet and an opposite side 16 of the sheet. The opposite side 16 may face orbital tissue, muscles, and other membranes.

Figure 2A:
FIG. 2A shows a top plan view of one embodiment of a surgical implant.
Figure 2B:
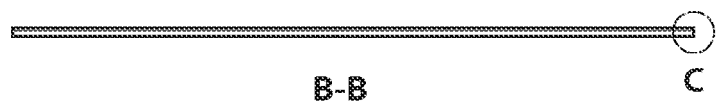
FIG. 2B shows a side plan, cross-sectional view of the surgical implant of FIG. 2A.
Figure 2C:
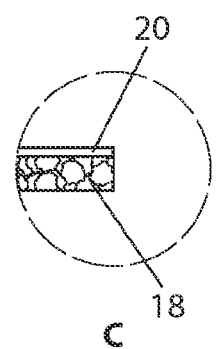
FIG. 2C shows a close-up, cross-sectional view of the surgical implant of FIG. 2A.

In one example, the bone-facing side 14 may have a porous surface and the opposite side 16 may have a solid (non-porous) surface. One example of an implant sheet 10 having this configuration is as shown by FIGS. 2A-2C. These figures illustrate a porous layer 18 and a solid (non-porous) layer 20. This implant may be referred to as a porous/solid implant sheet. In use, the porous side 18 of the implant sheet 10 may be positioned against the orbital bone of the patient. Without wishing to be bound to any theory, it is believed that the porosity of the bone-facing side 14 allows for tissue integration and ingrowth, which can help stabilize the implant sheet 10 in place. The solid side 20 (opposite the bone-facing side) provides a membrane layer that prevents the overlying tissue of the orbit from adhering thereto. Tissue may freely slide over the solid surface 20.

Figure 3:
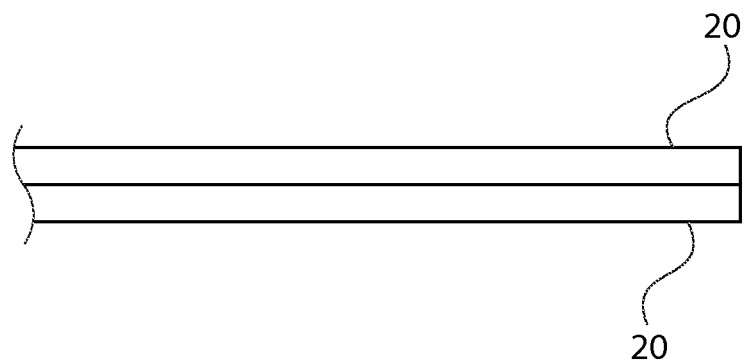
FIG. 3 shows a side plan view of an alternate embodiment of a surgical implant.
Figure 11:
FIG. 11 shows a side plan view of one embodiment of a three-part implant.

In another example, the bone-facing side 14 may have a solid (non-porous) surface and the opposite side 16 may also have a solid (non-porous) surface. This implant may be referred to as a solid/solid implant sheet. A solid/solid implant sheet may be preferred by some ocular surgeons, who are hesitant to provide any porous surfaces in the orbit. An example of this embodiment is illustrated by FIG. 3. Although this example does not provide a porous surface for tissue ingrowth, the implant sheet may be positioned similarly to the porous/solid implant sheet. Another example of a solid/solid implant sheet is illustrated by FIG. 11, which illustrates a porous sheet sandwiched between two solid membranes 32.

Figure 4:
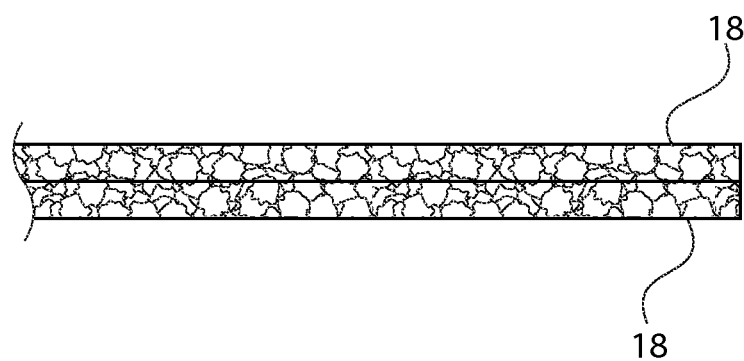
FIG. 4 shows a side plan view of an alternate embodiment of a surgical implant.
Figure 5:
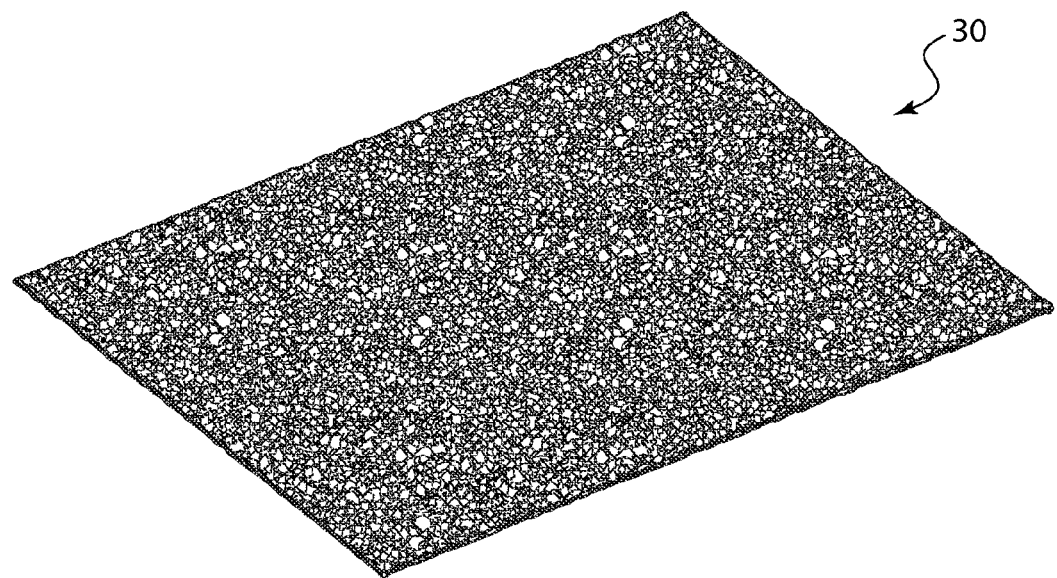
FIG. 5 shows a top perspective view of a porous sheet according to aspects of the disclosure.

In a further example, both surfaces of the implant sheet may be porous. This implant may be referred to as a porous/porous implant sheet. This implant sheet may be double-sided, as shown in FIG. 4. Such an implant may be formed by securing two porous layers to one another, typically via compression or heat bonding. In another example, the implant sheet may have a single layer, as shown in FIG. 5. Although unlikely to be desirable for use with orbital reconstruction, there are other surgeries in which such a porous/porous sided implant may be desirable.

In a further example, two implant sheets of varying porosities may be secured to one another, in an end to end configuration. This may result in a first portion having one porosity (or even a solid surface) with a second portion having a different porosity. The second portion of a different porosity may be used for bone or tissue ingrowth, while the first portion may be intended to provide a smooth surface that prevents bone or tissue ingrowth. The securement of the two implant sheets to one another may be via heat sealing, butt welding, thermal compression, or any other appropriate method. Non-limiting examples of implants having varying porosities on a single surface/face are illustrated by FIGS. 15-18 and 19. Further structural and manufacturing details for these examples are provided in more detail below.

It is also possible to form the implant sheets described herein by providing a first porous layer and loading additional materials or layers on the first porous layer in a mold. As heat is applied, the porous layer and additional materials or layers may form an implant sheet with multiple layers or materials compressed together. This may be referred to as compression molding. The result may be an implant sheet with differing thicknesses along one sheet. Non-limiting examples are illustrated by FIGS. 9-11, 13-14, and 19.

In another example, the result may be an implant sheet with dissimilar porosity regions having substantially equal thickness. The amount of material in each region of the sheet may be compressed, so that areas that contain more material produce a smaller pore size or a solid non-porous area. Again, further structural and manufacturing details for these examples are provided in more detail below. Other methods of attachment are possible and considered within the scope of this disclosure.

Implant Sheet.

In some examples, the implant sheet 10 comprises a thin sheet of a polymer. The polymer may be, but is not limited to, a polyolefin (such as polyethylene), polyether ether ketone (PEEK), polyethylene terephthalate (PTFE), nylon, polypropylene, or any polymer of aliphatic hydrocarbons containing one or more double bonds, composites of any of the above materials, or any other appropriate polymeric material. If the polymer is provided as a polyethylene, high density polyethylene or ultra high molecular weight polyethylene (UHMWPE) has been found useful. The polymers used are generally surgical grade polymers.

In most cases, the implant sheet 10 described herein is manufactured as a thin porous sheet 30. Embodiments may further include a solid surface (formed by a solid membrane 32) that is heat compressed to bond, adhere, or otherwise secure to one or both faces of the initial porous sheet 30 or to an edge of the thin porous sheet 30 (e.g., in an end to end welding or bonding). Accordingly, the thin porous sheet 30 may remain as a porous/porous sheet, it may be formed as a porous/solid sheet, or it may be formed as a solid/solid sheet. The following description provides methods for manufacturing the initial thin porous sheet 30. It should be understood, however, that other methods are possible and considered within the scope of this disclosure.

Figure 6:
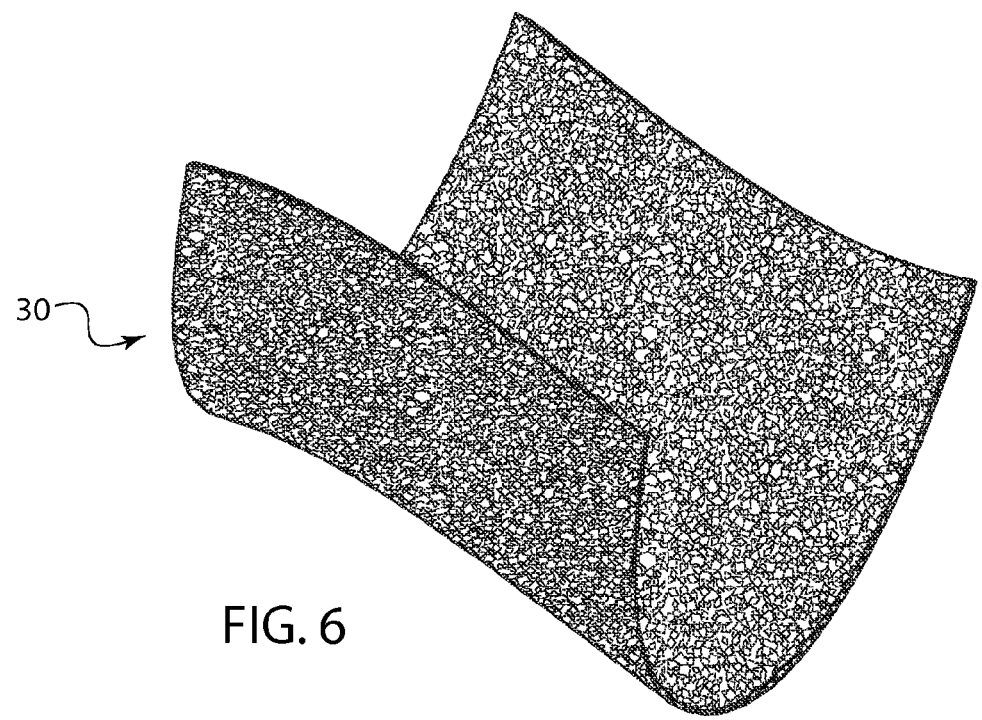
FIG. 6 shows a side perspective view of the porous sheet of FIG. 5 being folded.

One method for manufacturing a thin porous sheet 30 comprises coating a heated mandrel with a polymeric material. It is believed that producing a porous sheet on a heated mandrel can produce a sheet that is much thinner than traditional sheets, which are produced by filling a closed mold with polymeric material. Filling a mold with particles and applying heat thereto results in a sheet with tightly compacted particles. The resulting thickness is a sheet with multiple layers of the size of the particles used. Additionally, if a sheet produced by filling a mold with particles is compressed further, it may cause the sheet to become solid and lose its porosity. By contrast, the present inventor has found that heating particles on a heated mandrel provides a porous sheet having particles spaced more openly. This generally results in a substantially thinner porous sheet. In one example, the porous sheet may be a single particle thick. The porous sheet may be as thin as 0.25 mm. In fact, a single porous sheet manufactured using this method is comparable in flexibility to a piece of fabric that can be rolled as illustrated by FIG. 6, rather than a thicker, hardened sheet. The sheet may have an interconnected pore structure with an open pore structure having a pore volume in a 50% range. A specific range may be from 10-50% pore volume.

FIG. 6 illustrates the flexibility of a thin porous sheet 30 manufactured using this method. This thin porous sheet 30 may be compressed without causing the sheet to become solid and lose its porosity. Because the porosity is so high in the thin porous sheet 30, with the pores being large and spaced apart from one another, the resulting thin porous sheet 30 may be compressed without losing porosity. In one example, the porosity of the porous side of the thin porous sheet 30 may range from about 0.25 mm to about 3.0 mm. Specific embodiments may be about 0.35 mm, 0.45 mm, 0.85 mm, 1.5 mm and 3.0 mm.

Figure 7:
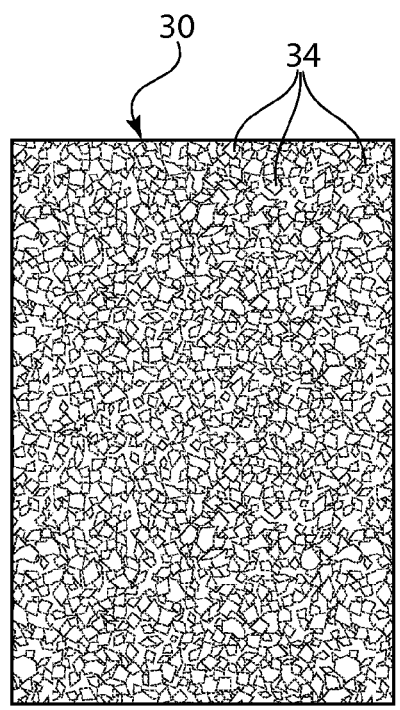
FIG. 7 shows a top plan view of a porous sheet prior to compression.
Figure 8:
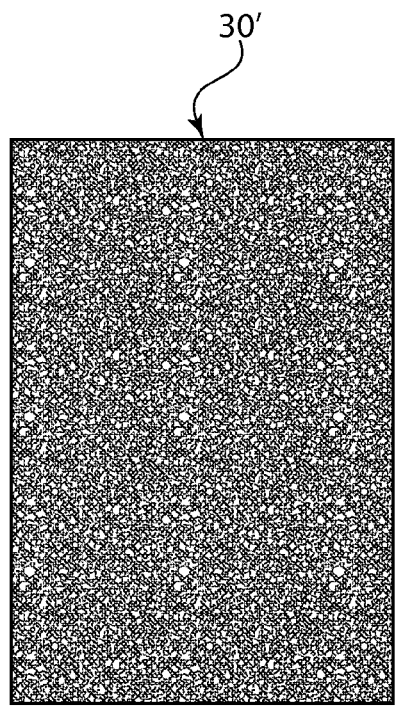
FIG. 8 shows a top plan view of the porous sheet of FIG. 7 after compression in a mold.

Upon compression (at a certain heat and at a certain level), the individual particles 34 of the thin porous sheet 30 may be compressed such that they merge closer to one another, but the pores do not close. This compression step may also result in an even thinner porous sheet. FIG. 7 illustrates a thin porous sheet 30 after being formed on a mandrel but before further processing. FIG. 8 illustrates the porous sheet after an additional heat compression step in a traditional mold. As shown, the pores may become smaller and more compressed, but they are still present. The thickness of the thin porous sheet 30 may range from about 0.25 mm to about 0.45 mm; from about 0.3 mm to about 0.6 mm; from about 0.35 mm to about 0.55 mm; from about 0.45 mm to about 0.65 mm; from about 0.5 mm to about 0.9 mm; and about 0.6 mm.

Lamination.

In a further example, the thin porous sheet 30 may be laminated with a solid membrane sheet. For example, a thin porous sheet 30 manufactured on a heated mandrel may be assembled with a solid membrane 32. The solid membrane 32 may be a solid sheet of the same polymer of the thin porous sheet 30. The polymer may be, but is not limited to, a polyolefin (such as polyethylene), polyether ether ketone (PEEK), polyethylene terephthalate (PTFE), nylon, polypropylene, or any polymer of aliphatic hydrocarbons containing one or more double bonds, composites of any of the above materials, or any other appropriate polymeric material. If the polymer is provided as a polyethylene, high density polyethylene or ultra high molecular weight polyethylene (UHMWPE) has been found useful. The polymers used are generally surgical grade polymers. The solid membrane 32 may be from about 0.004 inches thick to about 0.10 inch thick. Specific examples include 0.004 inches thick, 0.006 inches thick, 0.008 inches thick, and 0.010 inches thick.

Figure 9:
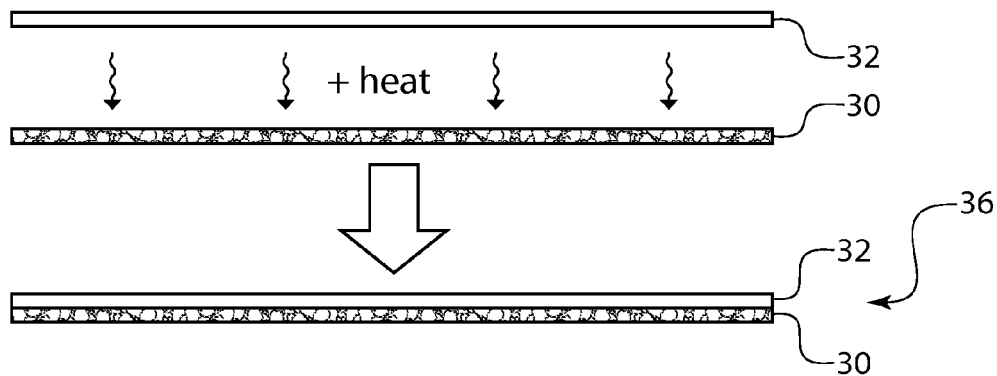
FIG. 9 shows a schematic of one method that may be used to create a surgical implant having a porous face and a solid face.

The solid membrane 32 may be applied to one or both faces of the thin porous sheet 30. In one example, the thin porous sheet 30 and the solid membrane 32 may be heat bonded together to produce a lamination article 36 that is porous on one side and solid on the other side. The solid membrane 32 may have similar dimensions to the thin porous sheet 30. FIG. 9 shows one example of this embodiment.

Figure 10A:
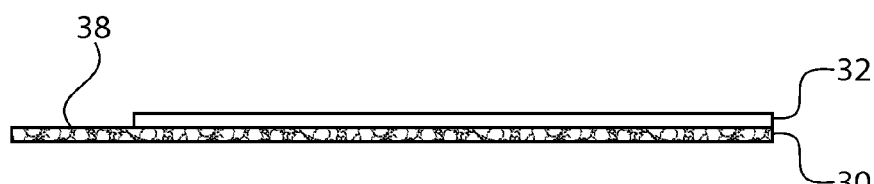
FIG. 10A shows a side plan view of an implant having a porous tab extending therefrom.
Figure 10B:
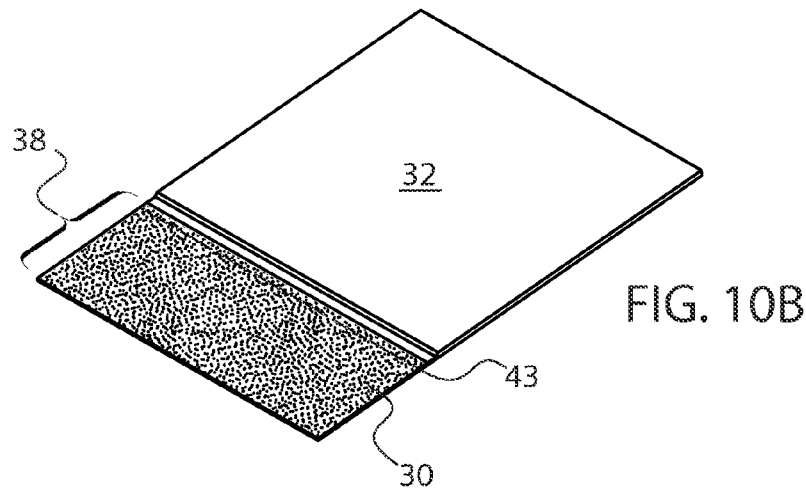
FIG. 10B shows a side perspective view of the implant of FIG. 10A.

In another example, the solid membrane 32 may have a length and/or width that is shorter than the thin porous sheet 30. This may result in a laminated article that has an extended porous tab 38. FIGS. 10A and 10B show one example of this embodiment. For example, the thin porous sheet 30 may be heat sealed or otherwise thermally bonded or compression molded to the solid membrane sheet 32. A thin porous sheet 30 of a first, longer length may have a solid membrane sheet 32 of a second, shorter length positioned thereagainst. Application of the heat to the two sheets 30, 32 may cause them to thermally bond to one another, with the longer thin porous sheet 30 extending therefrom. A registration line 43 may result, which distinguishes the porous sheet 30 from the solid membrane sheet 32.

In another example, the thin porous sheet 30 and two solid membranes 32 (one on each face of the thin porous sheet 30) may be heat bonded together to produce a lamination article 36 that is solid on both sides. FIG. 11 shows one example of this embodiment.

In a further example, it is possible for a thin porous sheet 30 to be manufactured on a mandrel, folded upon itself, and laminated or secondarily compressed to itself. The sheet 30 may be folded in half, the sheet 30 may be folded with only a lower portion folded upon the sheet 30 in order to create a laminated tab area at the folded portion, or any other portion of the sheet 30 may be folded. A heat treatment may be applied to thermally bond the folded portion to the remainder of the sheet portion.

By beginning with the thin porous sheet 30 formed on a heated mandrel, the additional heat bonding does not cause the porous side to lose its porosity. In one example, the thickness of the lamination article 36 may range from about 0.25 mm to about 0.9 mm. Specific ranges include from about 0.25 mm to about 0.45 mm; from about 0.3 mm to about 0.6 mm; from about 0.35 mm to about 0.55 mm; from about 0.45 mm to about 0.65 mm; from about 0.5 mm to about 0.9 mm; and about 0.6 mm.

Figure 12:
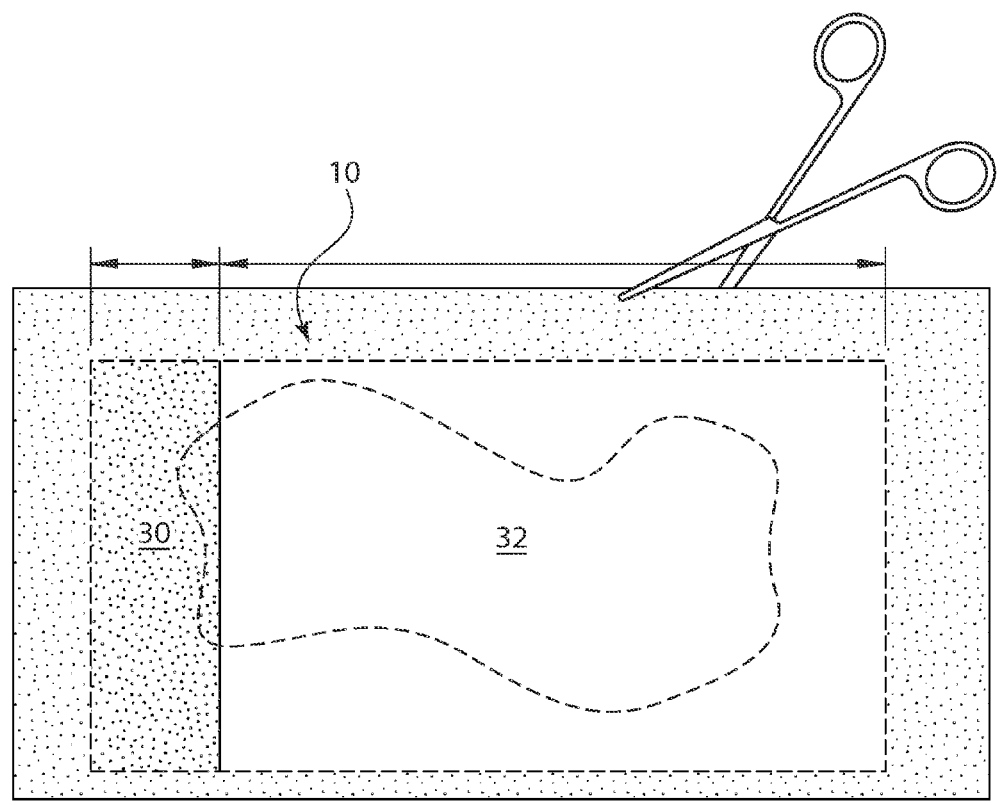
FIG. 12 shows a top plan view of a surgical implant, illustrating how a surgeon can cut the implant into a desired shape.

These thickness ranges provide an implant that is at least partially pliable, which is generally desirable during reconstruction surgery. The implant sheets may be trimmed using scalpels or scissors. For example, in a method of reconstruction, the implant sheet may be cut and shaped to conform to the profile of a defect to be treated. An example of an implant sheet being trimmed to a desired shape is illustrated by FIG. 12. The implant sheet may then be secured to bony tissue using surgical screws, sutures or any appropriate mechanical fastener.

Welding/Bonding End to End.

In other examples, the implant sheets described herein may have different porosities on the same side. It is possible to provide two implant portions that are bonded to one another, in an end to end configuration. Examples of implants manufactured using this method are illustrated by FIGS. 15-21. The implant portions used may generally have equal thicknesses, but dissimilar porosities. This can provide a finished implant that has two different porosities on the same side/surface. A first portion may have a first porosity (or be solid surface or a substantially solid surface), and a second portion may have a second porosity. If the first portion is a solid or substantially solid surface, the first portion would generally be intended to prevent or reduce tissue ingrowth. If the second portion is a porous/less solid layer, the second portion would generally allow or encourage tissue in growth. This provides an implant sheet 10 having a surface that is both solid and porous on the same face/surface. One of the portions may form a porous tab 38 that can be bent over the inferior rim of the orbit and sutured, screwed, or otherwise fastened or secured into place, in order to stabilize the implant. In one example, a tab 38 may be provided with one or more predetermined holes 40 in order to assist placement of the implant. (Pre-determined holes 40 are illustrated by the implants shown in FIGS. 13 and 14. It should be understood, however, that fingers and/or pre-determined holes may be provided on any other embodiments or examples described herein.)

In one specific example, a posterior portion of the implant may be solid, and an anterior portion of the implant may be porous. The anterior portion may form a porous tab 38, which can assist with securement of the implant sheet 10 over the bone edge of the orbit. The posterior portion may generally remain in the orbit area, impervious to tissue ingrowth. This configuration is illustrated by the implant of FIG. 1.

Figure 15:
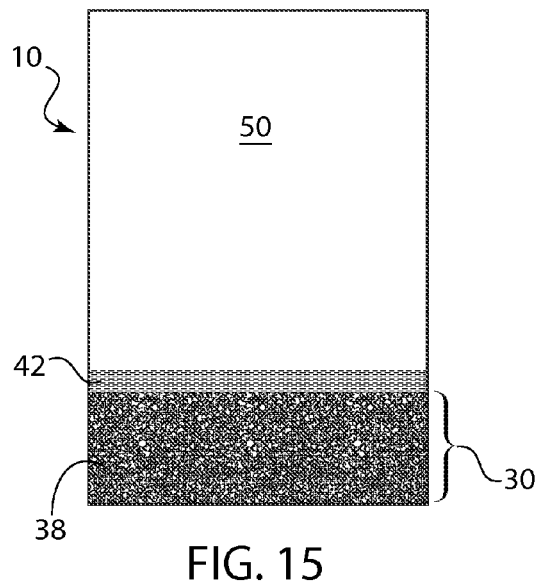
FIG. 15 shows a top plan view of an implant having two portions butt welded and/or thermally bonded to one another.
Figure 16:
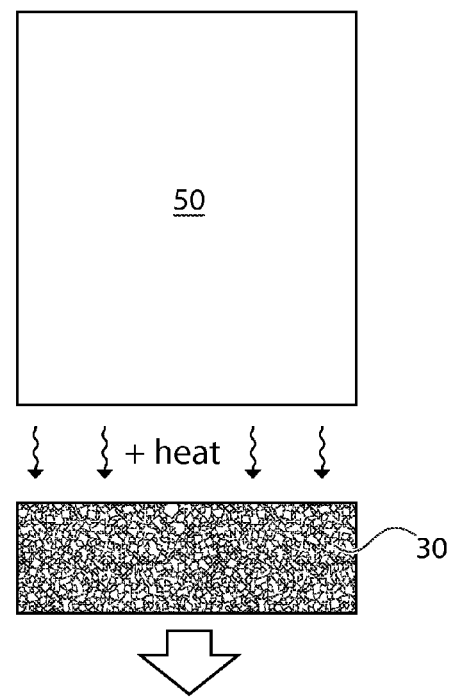
FIG. 16 shows a schematic illustrating one embodiment of a method for securing implant portions to one another.
Figure 17:
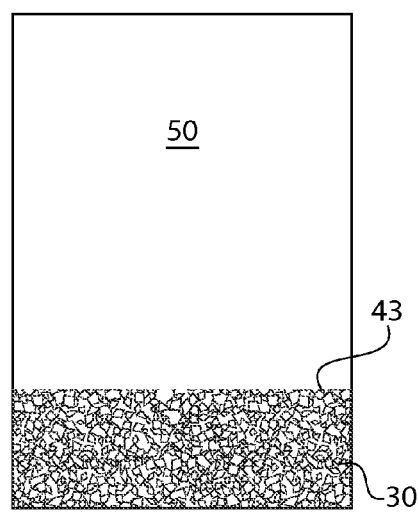
FIG. 17 shows a top plan view of an implant having two portions that are compressed or laminated to one another.

In another example, a strip of the thin porous sheet 30 may be thermally bonded to a separate solid membrane sheet 50. In a specific method, the thin porous sheet 30 may be butt welded to the solid membrane sheet 50, resulting in an attachment juncture line 42. For example, two different sheets 30, 50 may be butted together and thermally bonded to one another. A useful analogy is a plastic bag sealer, which can deliver heat to a selected area in order to form a line of melted plastic/seal. It may be impossible to isolate the porous area from heat, so as to maintain the desired porosity, so it may be possible that the juncture 42 may be less porous than the sheet 30. One example of such an attachment juncture line 42 is illustrated by FIG. 15. The attachment juncture line 42 is generally more flexible than the solid membrane sheet 50 and can be easily bent in order to shape the resulting implant sheet.

It is also possible for a thin porous sheet 30 to be compressed with a membrane sheet 50. The sheets 30, 50 may be positioned end to end (or even overlapping a desired amount) and compressed in a mold to form a junction line 43. This junction 43 may not be as distinct as attachment junction 42, but it is still possible to differentiate between the two portions.

Figure 21:
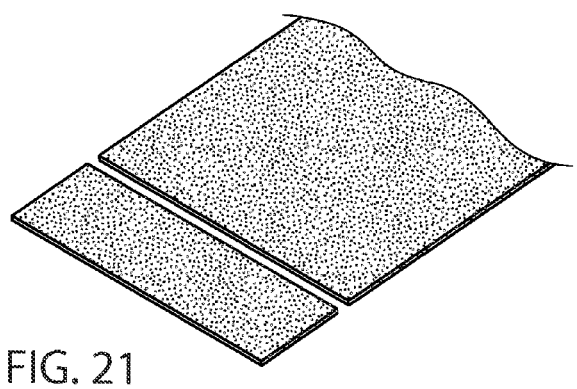
FIG. 21 shows a side perspective view of a method for securing two porous implant portions to one another.

It is also possible to join two different implant sheets that are both porous, but that have differing pore sizes. One example of this embodiment is illustrated by FIG. 21. This is an implant sheet having a surface that is porous/porous created by being joined as shown.

Secondary Compression.

In an even further example, the thin porous sheet 30 may be compressed with additional material in the mold. In one example, this may provide a product with a portion that remains porous and a portion that is solid/non-porous where the additional material is located. In another example, the thin porous sheet 30 may have only an upper portion thereof heat compressed by the mold, in order to provide a product with a portion that remains porous and a portion that is less porous (and depending upon the level of heat and compression used, that is non-porous). These examples provide a secondary compression. The thin porous sheet 30, after being formed, can be compressed with either additional particulate material to be formed or with a secondary sheet (either a thin porous sheet or a solid membrane). This may result in a product that has two layers that are pressed together. This may further result in a product that has portions of varying thicknesses. In other embodiments, this may result in a product that has a single thickness across the product. Examples are illustrated by FIGS. 13, 14, and 18-20.

Figure 13:
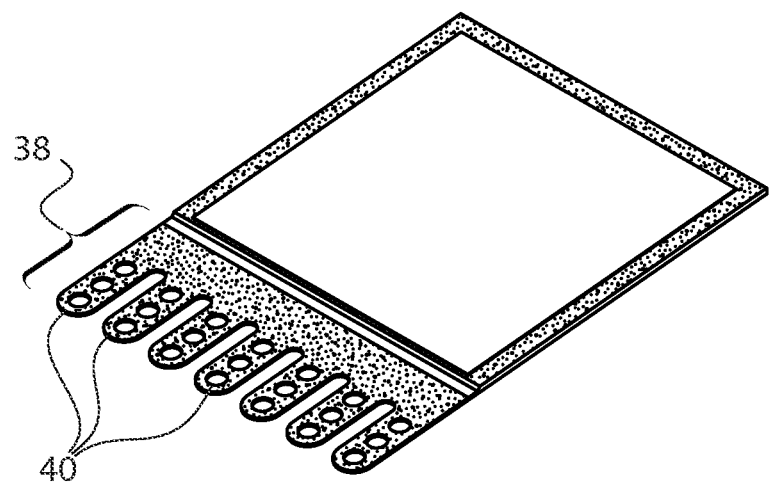
FIG. 13 shows a side perspective view of one embodiment of an implant, having a porous tab with extending fingers.
Figure 14:
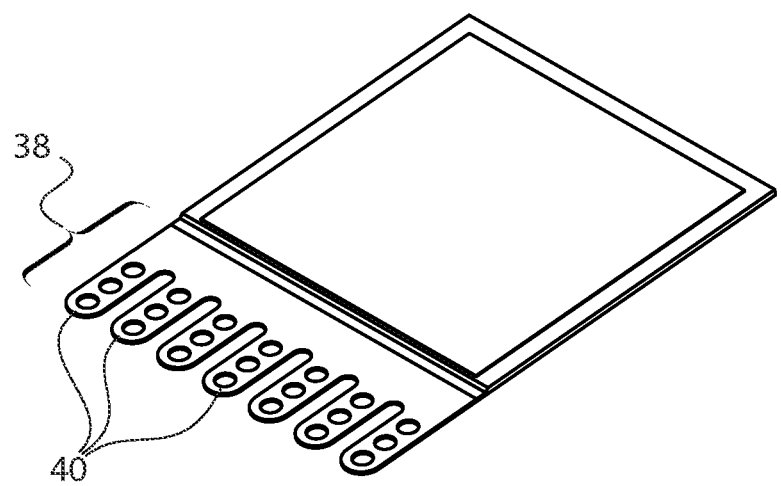
FIG. 14 shows a side perspective view of one embodiment of an implant, having a solid tab with extending fingers.
Figure 18:
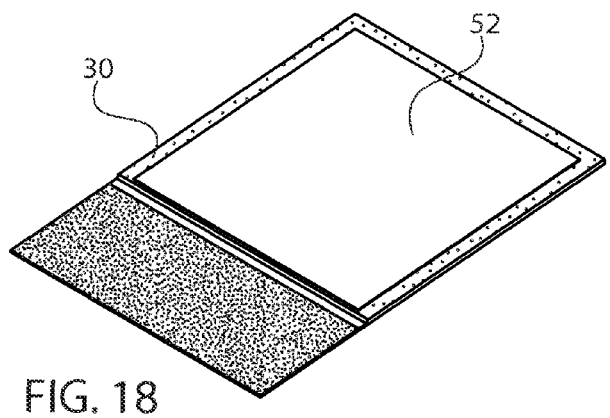
FIG. 18 shows a side perspective view of an implant having a solid membrane portion, a porous sheet portion of a first porosity, and a second porous sheet portion of a different porosity.
Figure 19:
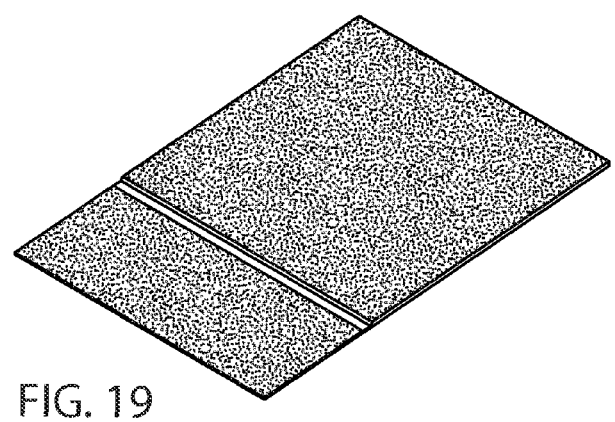
FIG. 19 shows a side perspective view of an implant having first and second porous sheet portions, which may be of varying porosities.
Figure 20:
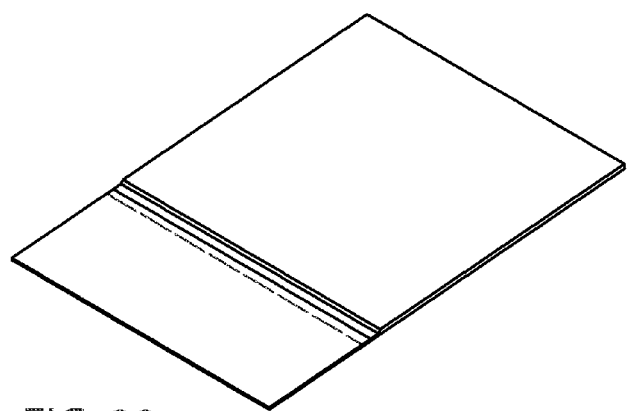
FIG. 20 shows a side perspective view of a solid/solid welded implant.

FIG. 13 illustrates a thin porous sheet 30 with a tab 38 formed with fingers having openings 40 therein. This may assist with securement of the implant sheet in place. The thin porous sheet 30 has a membrane 52 positioned thereover. The tab portion 38 may be the same porosity or a different porosity from the thin porous sheet. FIG. 14 illustrates a solid membrane sheet with another solid membrane sheet positioned thereover. This embodiment also has a tab 38 formed with fingers having openings 40 therein. The tab may be porous or non-porous. FIG. 18 illustrates a thin porous sheet 30 with additional materials 52 positioned thereover, which, in one embodiment, may be a porous sheet of a differing porosity and a solid membrane sheet. FIG. 19 illustrates a thin porous sheet with additional materials positioned thereover, which, in one embodiment, may be another thin porous sheet. FIG. 20 illustrates a solid membrane/solid membrane embodiment, with a weld portion therebetween.

In another example, the solid membrane sheet 50 portion of the implant may be produced by using compression molding of a specified area of a single thin porous sheet 30. This may result in the non-compressed portion of the sheet 30 remaining porous, and the compressed portion of the sheet 30 being formed into a solid membrane sheet 50. The resulting implant may resemble the one shown in FIG. 16, 17, or 18. A registration line 43 may result which distinguishes the porous portion from the solid portion. The result may be an implant that has dissimilar porosity regions with generally substantially equal thicknesses. While the amount of material in each region of the sheet may be controlled and subsequently compressed, areas containing more material may produce a smaller pore size (or even a solid, nonporous area).

Figure 22:
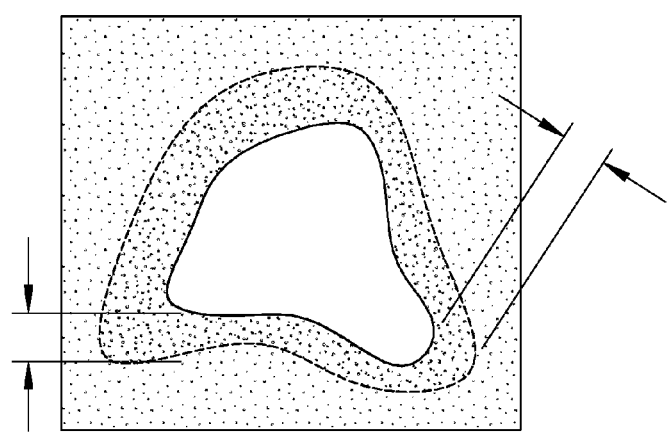
FIG. 22 shows a top plan view of a porous sheet that has been secondarily compressed with additional material applied in a desired shape.

For example, the shape of a desired region may be produced by the shape and amount of materials loaded on the thin porous sheet, thus resulting in differing bulk density in the desired region. One example of such an implant is illustrated by FIG. 22. The materials may be formed in the desired shape, and the final implant may be cut to an even more specific shape by the surgeon. In another embodiment, the shape of the desired region may be produced by stacking multiple layers of material in a mold. Areas that are to have a greater bulk density (i.e., which may be a solid layer) may start with more material, and areas that are to have a lesser (i.e., a porous layer) may start with less material. In a specific embodiment, the beginning material is loaded into a tool in the form of substantially thin layers of porous material formed on a mandrel.

In another embodiment, the sheet may be created by separate porous articles or porous sheets that are inserted into a mold cavity and thermally processed. A secondary molding operation may act upon the sintered porous particles causing the surface pores of the sheet to become compressed together, producing a smooth surface with large internal pores for improved tissue ingrowth. The final shape of the sheet may be produced by compression and thermal processing. In one embodiment, the final shape may be fitted as an orbital floor sheet. The sheet may also contain a line or junction that differentiates the less porous or solid layer from the porous layer. This line may be used as a registration point, offset from the intended cut location to produce a specified length of the section being trimmed to a desired size by cutting, for example. Examples are illustrated by FIGS. 12 and 22.

The intersection of the two differing areas may be visible. The area that is less porous to solid, and the area that is more porous produce a visible point of their intersection. Compression joining methods and/or secondary compression may provide a juncture 43 that may be less distinct than the butt welded juncture 42. The intersection line, or shape, can be aligned with a registration feature of a fixture to allow for cutting/trimming of the implant, producing a specified length from the intersection line or shape. In a two-dimensional pattern, the pattern or line is visually aligned to a registration feature of a cutting fixture, that in turn has a cutting edge or pattern intended to produce the shape or size of the cut piece. This use of the registration feature allows the intersection of the two differing areas of the implant to be determined in the resulting cut pattern. Examples are illustrated by FIGS. 12 and 22.

The thicknesses of the implant sheets 10 used may range from about 0.10 mm to about 3.0 mm. In more specific examples, the thicknesses may range from 0.12 mm to about 0.25 mm; from 0.2 mm to about 0.5 mm; from about 0.3 mm to about 0.6 mm; from about 0.3 mm to about 0.75 mm; from about 0.5 mm to about 1.0 mm; from about 0.75 mm to about 2.0 mm; from about 1.0 mm to about 3.0 mm. These examples are provided for description purposes only, and are not intended to be limiting in any way.

Although the orbital floor sheet described herein has been described in relation to its use for orbital floor reconstruction, it should be understood that the implant sheets may be used for a number of other reconstructive surgeries for other anatomical parts.

The headings used herein and for reference only, and are not intended to be limiting in any way. Changes and modifications, additions and deletions may be made to the structures and methods recited above and shown in the drawings without departing from the scope or spirit of the disclosure or the following claims.

What is claimed is:

1. A surgical implant, comprising:
   a porous sheet comprising a layer of a polymeric material that is about 0.25 to about 0.60 mm thick, such that the porous sheet is flexible and pliable, the porous sheet having an interconnected pore structure that may be compressed by a heat compression mold without losing porosity; and
   a solid membrane sheet attached to at least one side or edge of the porous sheet,
   wherein the solid membrane sheet has a thickness ranging from about 0.004 to about 0.010 inches.

2. A surgical implant, comprising:
   a porous sheet comprising a layer of a polymeric material that is about 0.25 to about 0.60 mm thick, such that the porous sheet is flexible and pliable, the porous sheet having an interconnected pore structure that may be compressed by a heat compression mold without losing porosity; and
   a solid membrane sheet attached to at least one side or edge of the porous sheet,
   wherein the porous sheet comprises an upper surface and a lower surface, and wherein the solid membrane sheet is applied to one or both of the upper surface or lower surface,
   wherein the solid membrane sheet is shorter than the porous sheet, such that the implant comprises an extended porous tab.

3. A surgical implant, comprising:
   a porous sheet comprising a thickness of from about 0.25 mm to about 0.60 mm, the porous sheet manufactured by heating polymeric particles on a mandrel to form an interconnected pore structure that may be compressed by a heat compression mold without losing porosity,
   further comprising a solid membrane sheet butt-welded to an end of the porous sheet,
   providing an implant that is both porous and non-porous on a single surface.

4. The surgical implant of claim 3, further comprising an attachment juncture line where the porous sheet and the solid membrane are bonded.

5. A surgical implant, comprising:
   a porous sheet comprising a thickness of from about 0.25 mm to about 0.60 mm, the porous sheet manufactured by heating polymeric particles on a mandrel to form an interconnected pore structure that may be compressed by a heat compression mold without losing porosity,
   wherein at least a portion of the porous sheet is secondarily compressed to itself.

6. A surgical implant, comprising:
   a porous sheet comprising a thickness of from about 0.25 mm to about 0.60 mm, the porous sheet manufactured by heating polymeric particles on a mandrel to form an interconnected pore structure that may be compressed by a heat compression mold without losing porosity,
   wherein the porous sheet is secondarily compressed with additional material in a mold to provide an implant with multiple layers that are compressed together.

7. A surgical implant, comprising:
   a porous sheet comprising a thickness of from about 0.25 mm to about 0.60 mm, the porous sheet manufactured by heating polymeric particles on a mandrel to form an interconnected pore structure that may be compressed by a heat compression mold without losing porosity, wherein the porous sheet is secondarily compressed with a secondary porous sheet or solid membrane sheet to provide an implant with two layers that are compressed together.

* * * * *